United States Patent [19]
Carney

[11] Patent Number: 5,368,040
[45] Date of Patent: Nov. 29, 1994

[54] APPARATUS AND METHOD FOR DETERMINING A PLURALITY OF HEMODYNAMIC VARIABLES FROM A SINGLE, CHRONICLALY IMPLANTED ABSOLUTE PRESSURE SENSOR

[75] Inventor: James K. Carney, Eden Prairie, Minn.

[73] Assignee: Medtronic, Inc., Minneapolis, Minn.

[21] Appl. No.: 100,881

[22] Filed: Aug. 2, 1993

[51] Int. Cl.5 ............................................. A61B 5/0205
[52] U.S. Cl. ........................................ 128/700; 128/672
[58] Field of Search ................ 128/670, 672, 673, 700

[56] References Cited

U.S. PATENT DOCUMENTS

| | | | |
|---|---|---|---|
| 3,893,452 | 7/1975 | Birnbaum | 128/673 |
| 3,939,824 | 2/1976 | Arneson et al. | 128/672 |
| 4,137,910 | 2/1979 | Murphy | 128/700 |
| 4,203,451 | 5/1980 | Panico | 128/672 |
| 4,257,423 | 3/1981 | McDonald et al. | 128/419 |
| 4,379,457 | 4/1983 | Stein | 128/419 |
| 4,407,296 | 10/1983 | Anderson | 128/675 |
| 4,432,372 | 2/1984 | Monroe | 128/675 |
| 4,485,813 | 12/1984 | Anderson et al. | 128/675 |
| 4,556,063 | 12/1985 | Thompson et al. | 128/419 |
| 4,677,984 | 7/1987 | Sramgk | 128/700 |
| 4,858,615 | 8/1989 | Meinema | 128/672 |
| 4,986,270 | 1/1991 | Cohen | 128/419 |
| 5,127,404 | 7/1992 | Wybomy et al. | 128/419 |

*Primary Examiner*—William E. Kamm
*Attorney, Agent, or Firm*—Harold R. Patton

[57] ABSTRACT

A method and apparatus for monitoring and measuring the hemodynamic status of a patient's pulmonary pressure and right atrial pressure. The aforementioned is achieved by using an implanted absolute pressure sensor located in the right ventricle, coupled to an implantable monitoring device, which records pressure values in response to a combination of sensed electrical depolarizations of the atrium and ventricle and occurrence of first and second derivatives of the pressure signal having values less than zero.

6 Claims, 6 Drawing Sheets

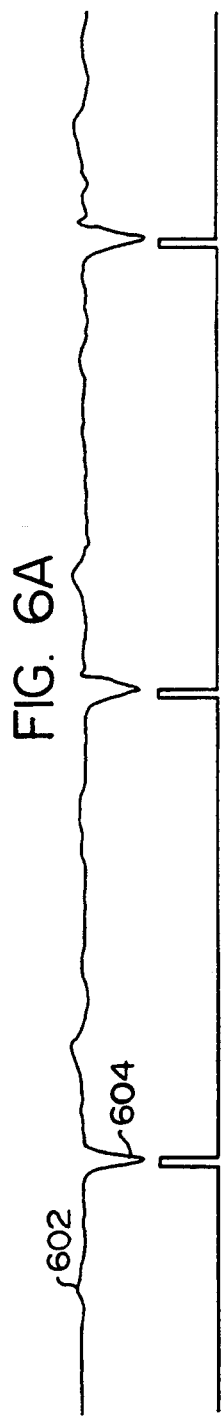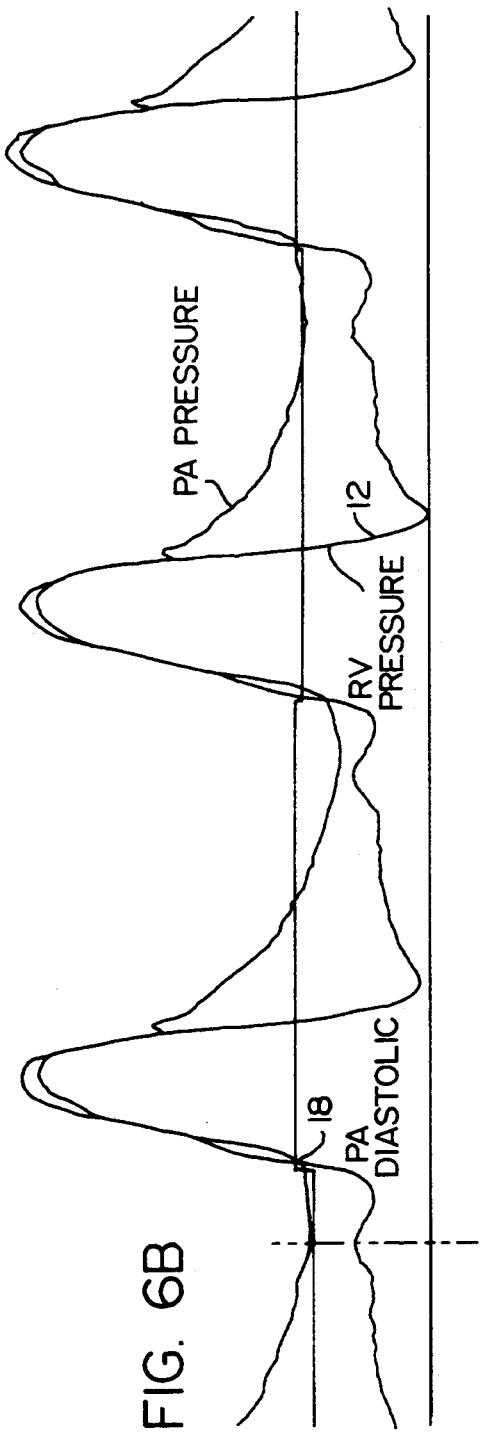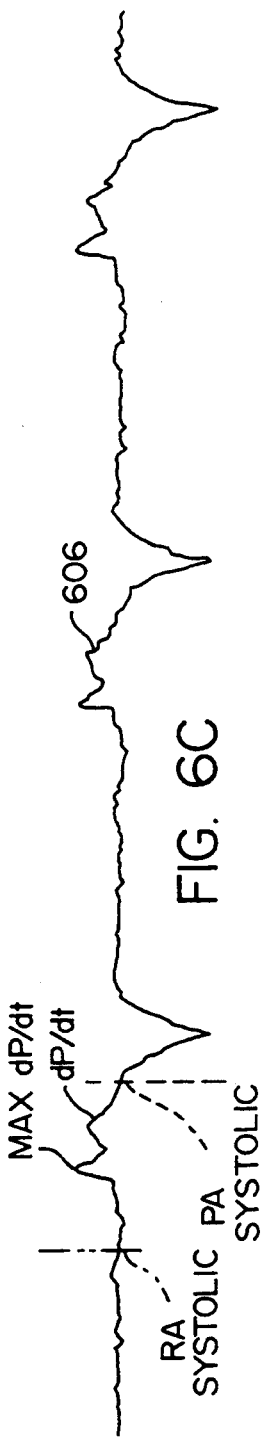

APPARATUS AND METHOD FOR DETERMINING A PLURALITY OF HEMODYNAMIC VARIABLES FROM A SINGLE, CHRONICLALY IMPLANTED ABSOLUTE PRESSURE SENSOR

BACKGROUND OF THE INVENTION

1. Field of the Invention

This invention relates to implantable medical devices, and more specifically, relates to chronically implantable devices for determination of a plurality of hemodynamic variables including but not limited to right atrial pressure and pulmonary arterial pressure.

2. Description of the Prior Art

Intravascular pressure sensors are known in the art. U.S. Pat. No. 4,407,296 issued to Anderson teaches a chronically implantable pressure transducer suitable for use in the cardiovascular system. A pressure transducer with an improved electronic circuit is taught in U.S. Pat. No. 4,432,372, issued to Monroe. A further improved pressure transducer is taught in U.S. Pat. No. 4,485,813, issued to Anderson et al. These pressure sensors have been directed to the control of artificial cardiac pacers using algorithms which convert measurements of pressure or change of pressure into pacing rate.

Increases in the complexity of pacemakers and other implantable medical devices have increased efforts at producing sensors and transducers to monitor a variety of physiologic functions. Such transducers allow the exploitation of the additional capability of such medical devices.

The measurements of pressures (particularly pulmonary wedge pressure and central venous pressure) inside the heart are typically used to determine the health of the patient and provide a proper therapy. A number of restrictions are placed on defining the approach to a chronically implantable pressure sensor. Three of these restrictions are:

(1) it is generally unacceptable to implant any hardware on the left side of the heart, so pressures are normally measured from the right side, (2) a chronic wedge pressure measurement is unacceptable due to pulmonary infarction, and (3) chronically implanted leads in the pulmonary artery have not yet been proven to be safe.

One system for treating a malfunctioning heart based on hemodynamics i.e., the pressure at a site in a patient's circulatory system is taught in U.S. Pat. No. 4,986,270 issued to Cohen.

None of these references teaches the use of a single chronically implanted absolute pressure sensor in the right ventricle for determining a plurality of hemodynamic variables, i.e., right atrial pressure, right ventricular pressure, and pulmonary arterial pressure in a patient.

SUMMARY OF THE INVENTION

The present invention is a method and apparatus to determine the hemodynamic status of a patient from measurements of pulmonary pressure and right atrial pressure obtained from a single absolute pressure sensor implanted in the right ventricle. Both of these values have been shown to correlate with the degree of cardiac failure of a patient. The inventive technique employs continual monitoring of the right ventricular pressure using an absolute pressure sensor and marking the right ventricular pressure at the moment of specific events.

When the pulmonary valve is open during right ventricular systole, the pressure in the right ventricle is nearly identical to the pulmonary arterial pressure. Therefore, pulmonary artery systolic pressure equals right ventricle systolic pressure. This pressure can be determined using the right ventricular pressure by: pulmonary artery (PA) systolic pressure=right ventricle (RV) pressure at the time $dP_{Rv}/dt=0$ during ventricular systole.

The pulmonary artery diastolic pressure is similarly determined from the right ventricle. As long as the pulmonary artery pressure is higher than the right ventricle pressure, the pulmonary valve is closed. As the ventricle begins to contract during systole, however, the right ventricle pressure surpasses the pulmonary artery pressure and the valve opens. The pressure in the pulmonary artery at the time the valve opens is the lowest pressure seen by the pulmonary artery and, therefore, is the pulmonary artery diastolic pressure. Thus, the pulmonary artery diastotic pressure is the pressure in the right ventricle at the moment the pulmonary artery valve opens. The time at which the valve opens has been shown to be nearly identical to the time of maximum dPRv/dt. Therefore, in one preferred embodiment, the pulmonary artery diastolic pressure can be determined using right ventricular pressure by: PA diastolic pressure=RV pressure at the time $d^2P_{RV}/dt^2=0$ at the start of systole.

In another preferred embodiment, the pulmonary artery diastolic pressure can be determined directly using right ventricular pressure at the requisite moment determined with the aid of ultrasound measurements.

In a further preferred embodiment, the pulmonary artery diastolic pressure can be determined with the aid of acoustic signature measurements to determine the precise moment in time that the right ventricular pressure is equivalent to the pulmonary artery diastolic pressure.

In yet another preferred embodiment, the precise moment for determining the validity of the pulmonary artery diastolic pressure can be determined by impedance change measurements performed on the patient.

From the above discussion, it is apparent that numerous ways and methods can be used to determine the precise moment in time when the pulmonary valve opens. Therefore, the present invention, although discussed in terms relating to calculation of derivatives of ventricular pressure measurements, is not so limited.

Right atrial systolic and diastolic pressure can also be determined from an absolute pressure sensor in the right ventricle with the present inventive apparatus and method. This is possible because the valve between the right atrium and right ventricle is open at all times except during right ventricular contraction. Therefore, the atrial diastolic pressure is the same as the right ventricular pressure just prior to atrial contraction (atrial pulse or P-wave sense). Atrial systolic pressure can be determined in much the same way as pulmonary artery systolic pressure. In this case however, the inventive apparatus must find $dP/dt=0$ after the start of atrial systole.

The present invention is applicable anywhere that the measurement of hemodynamic status is important, and includes, but is not limited to the diagnosis of the severity of congestive heart failure, pulmonary artery disease, and pulmonary hypertension or the measurement of hemodynamic variables like vascular resistance, contractility, etc. For example, the maximum dP/dt signal derivation capability of the present invention can also approximate contractility; and the RV diastolic pressure in combination with mean arterial pressure (e.g. measured by a cuff) and a separate measure of cardiac output (measured either invasively or noninvasively) can provide a measure of vascular resistance.

Other features and advantages of the present invention will be set forth in, or become apparent from, the following description and claims and illustrated in the accompanying drawings, which disclose by way of example and not by way of limitation, the principle of the invention and the structural implementation of the inventive concept. For example, the present invention can be used to control devices that provide therapy i.e., cardiac pacemakers, defibrillators or drug pumps.

BRIEF DESCRIPTION OF THE DRAWINGS

FIG. 6A illustrates an actual patient cardiac waveform of an ECG signal.

FIG. 6B illustrates actual patient cardiac waveforms of pulmonary artery pressure and right ventricular pressure signals.

FIG. 6C illustrates a waveform resulting from the derivative (dP/dt) of the right ventricular pressure signal depicted in FIG. 6C.

DETAILED DESCRIPTION OF THE PREFERRED EMBODIMENTS

Figure 1:
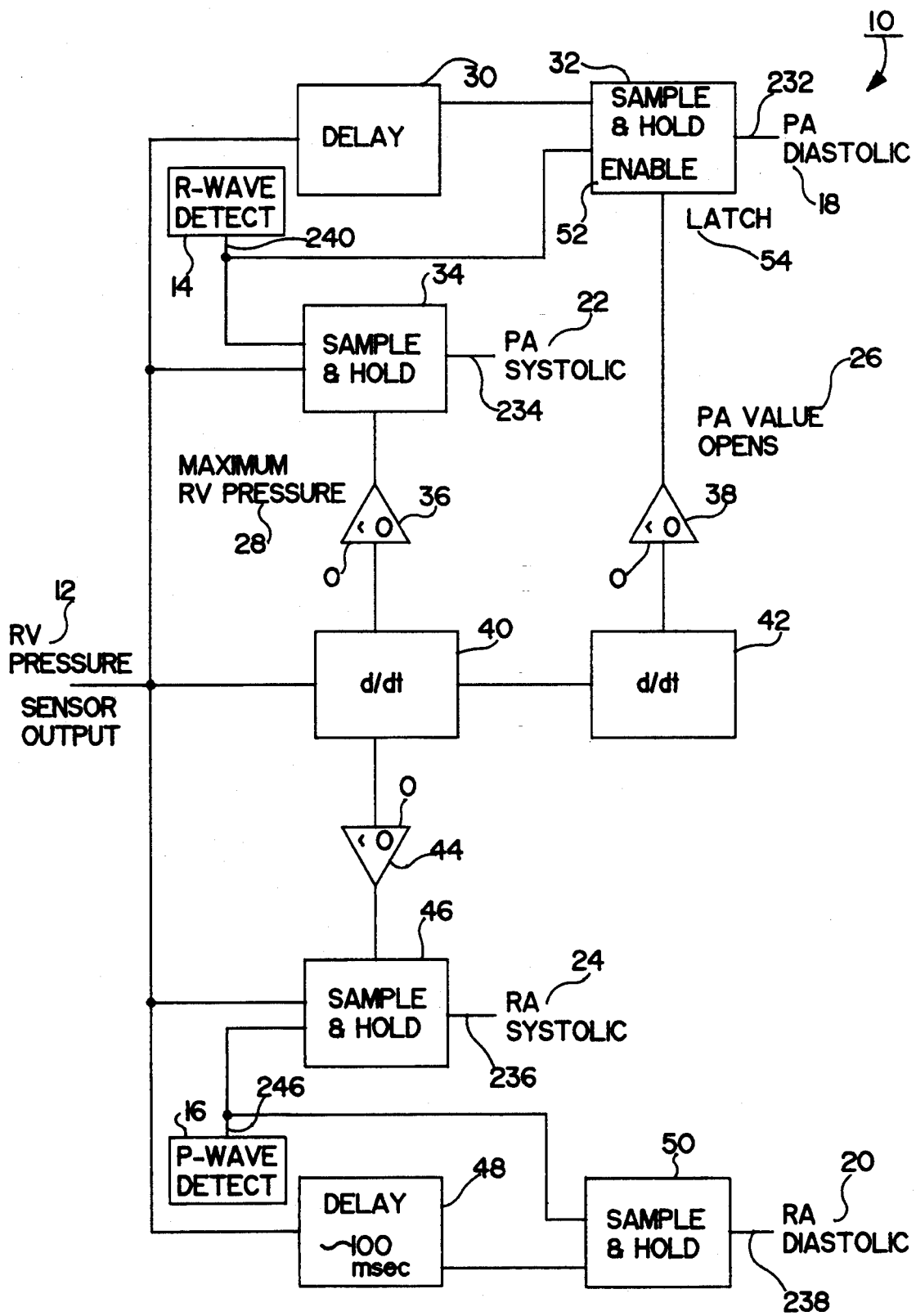
FIG. 1 is a partially block, schematic diagram of a control system, responsive to a right ventricular pressure sensor signal, an ECG R-wave signal and an ECG P-wave signal.
Figure 2:
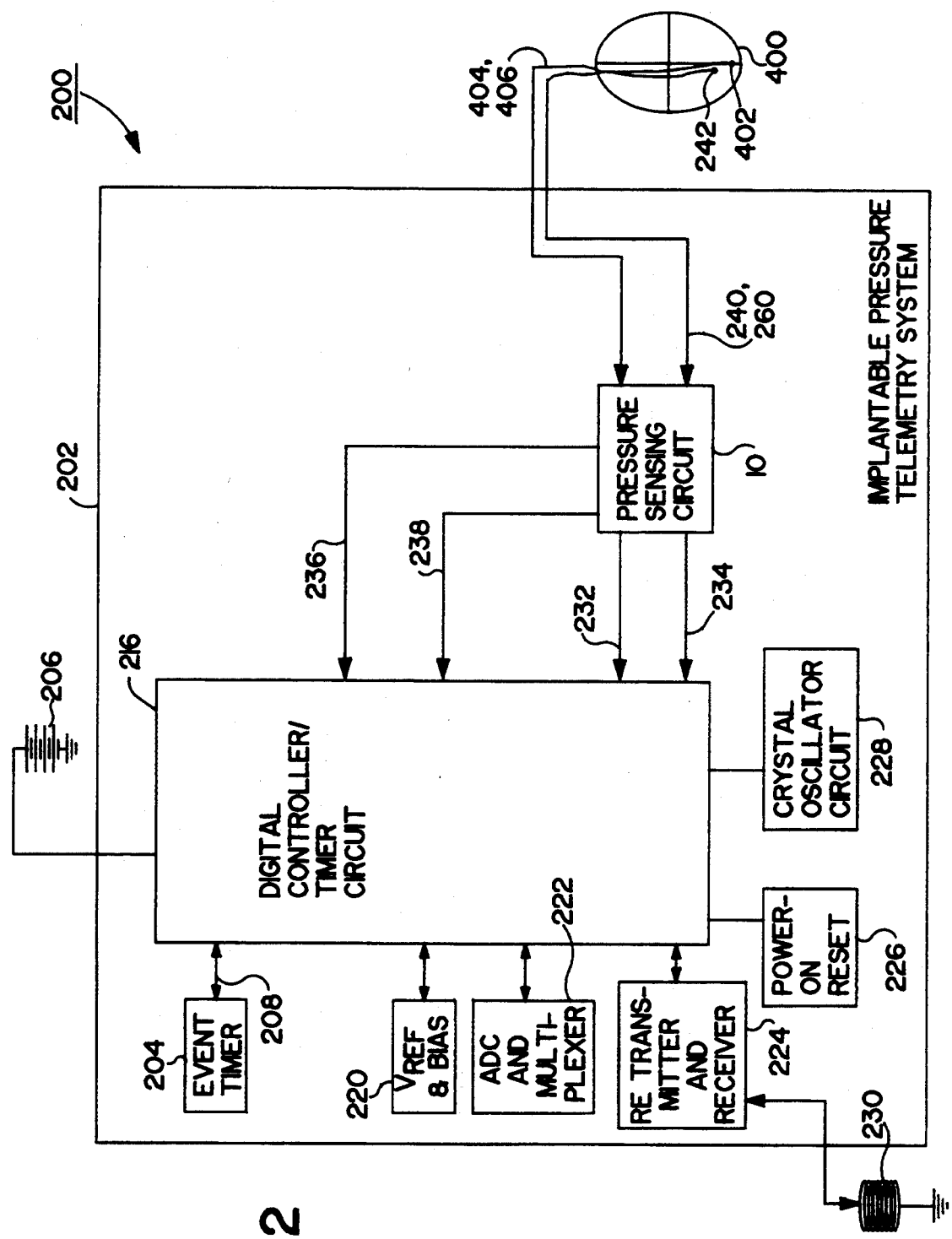
FIG. 2 is a block diagram of an implantable telemetry system which incorporates the control system of FIG. 1.
Figure 3:
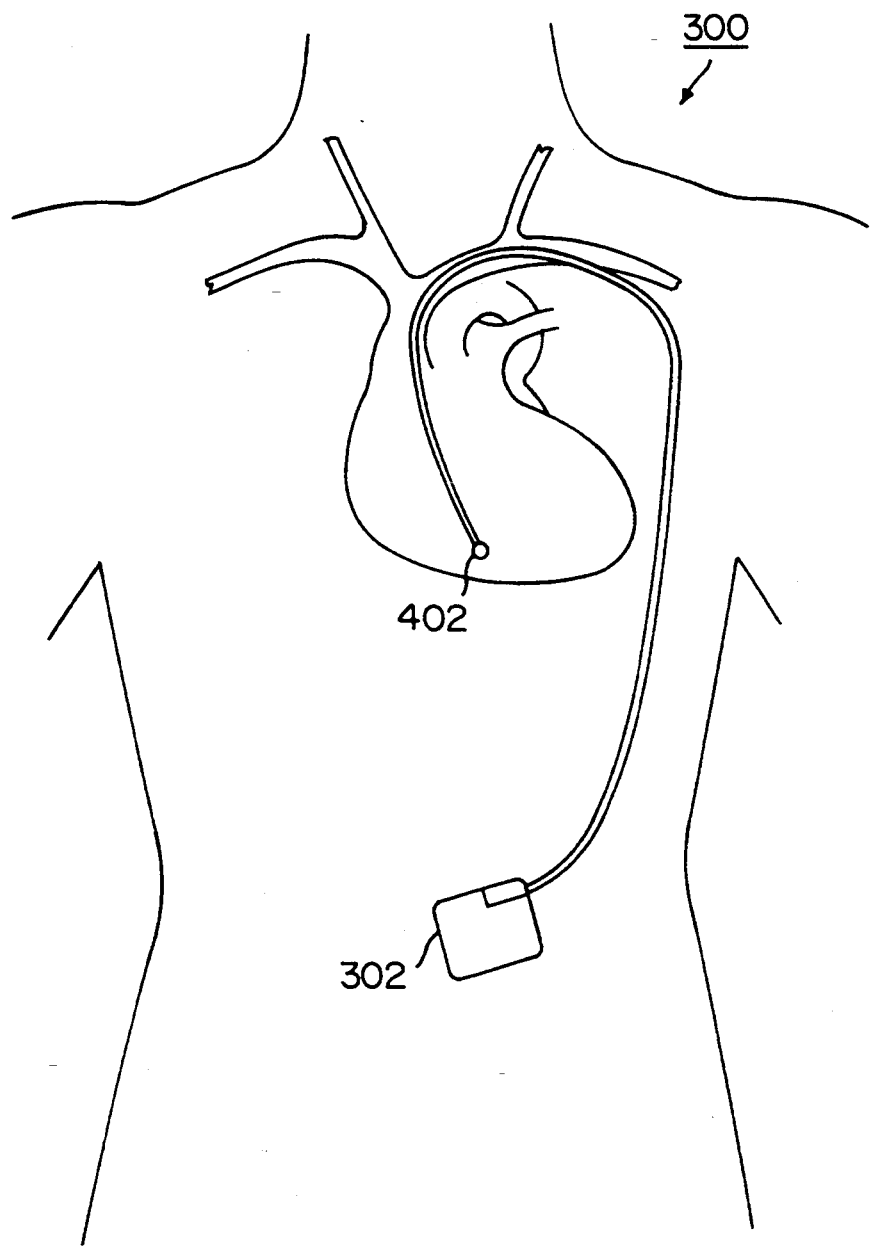
FIG. 3 is a diagrammatic, generalized illustration of an exemplary, right ventricular, implanted absolute pressure sensor and an associated telemetry device such as that illustrated in FIG. 2.
Figure 4:
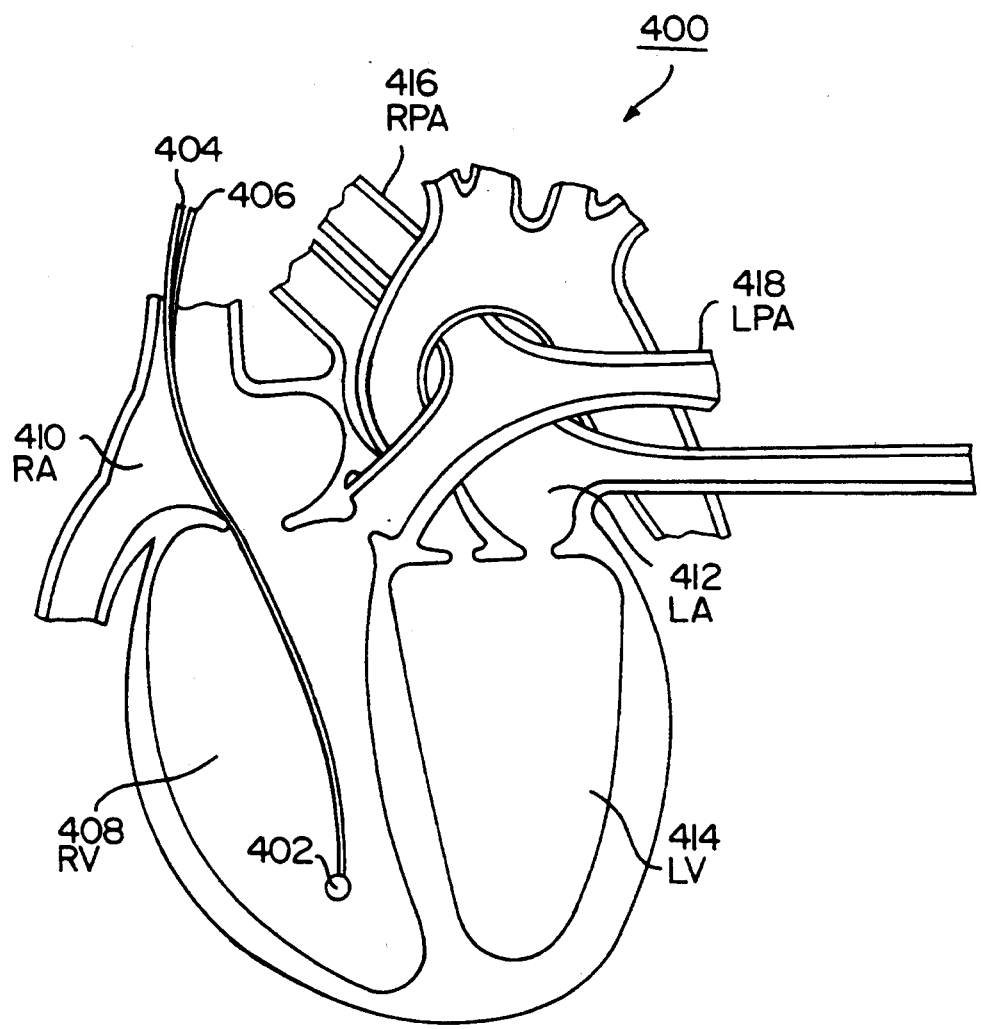
FIG. 4 is an illustration of an absolute pressure sensor positioned within a heart.

Starting generally with FIG. 1, there is depicted one embodiment of a pressure sensing circuit 10 which forms part of an implantable monitoring device 302 illustrated in FIG. 3 and used for determining the hemodynamic status of a patient. It is to be understood that device 302 is contained within a hermetically-sealed, biologically inert outer shield or "can", in accordance with common practice in the art. The sensing circuit 10 is operable in conjunction with an implantable absolute pressure sensor 402 which is implanted in the patient's right ventricle as depicted in FIG. 4. Implantable monitoring device 302 includes pressure sensing circuit 10 as well as additional control, power, memory and transmission circuitry illustrated in FIG. 2 and hereinafter discussed in detail.

Operation of the implantable monitoring device 302 will now be discussed in more detail with reference to FIGS. 1-6. As stated hereinbefore, the measurements of pressures, particularly pulmonary wedge pressure inside the heart are typically used to determine the health of a patient and provide a proper therapy. One illustrative method for determining pulmonary artery and right arterial diastolic and systolic pressure begins with reference to the simplified block diagram of pressure sensing circuit 10 illustrated in FIG. 1. The basic functional components are differentiators 40,42, comparators 36,38,44, sample-and-holds 32,34,46,50, and delays 30,48. Embodiment 10 also requires the output 14 from an R-wave sense amplifier ( not illustrated in FIG. 1) and the output 16 from a P-wave sense amplifier (not illustrated in FIG. 1), but known to those skilled in the art of cardiac pressure monitoring.

Figure 5A:
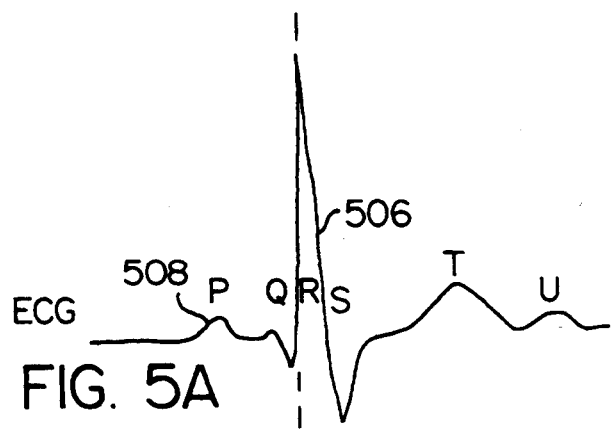
FIG. 5A illustrates a typical ECG signal.
Figure 5B:
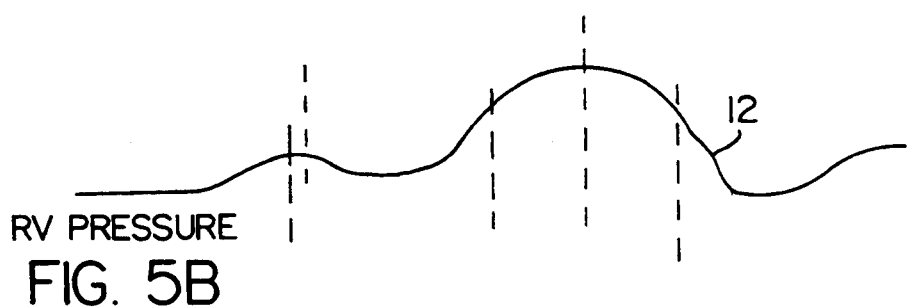
FIG. 5B illustrates a typical right ventricular pressure signal.
Figure 5C:
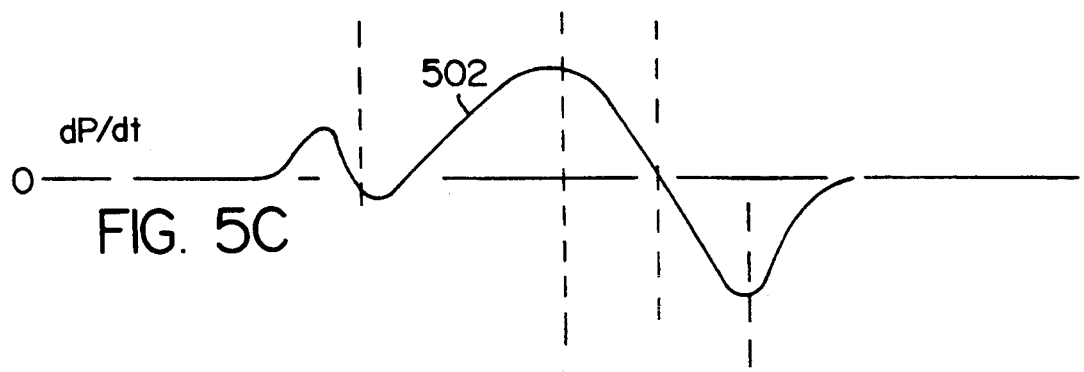
FIG. 5C illustrates a signal derived from the derivative of the signal depicted in FIG. 5B, and which can be used to determine pulmonary artery systolic pressure as well as right atrial systolic and diastolic pressure.

Operation of the preferred embodiment 10 shown in FIG. 1 begins by twice differentiating the signal 12 from an absolute pressure sensor 402 which is chronically implanted in the right ventricle, to provide dP/dt and $d^2P_{RV}/dt^2$. A typical ECG signal is illustrated in FIG. 5A while its associated right ventricular (RV) pressure sensor waveform 12 is shown in FIG. 5B. Differentiator 40 provides an output signal 502 illustrated in FIG. 5C which is the first derivative of waveform 12. Differentiator 42 provides an output signal 504 illustrated in FIG. 5D which is the second derivative of waveform 12.

Looking at the waveforms shown in FIGS. 5A-5D, it can be seen that the maximum RV (and PA) systolic pressure occurs the first time after the R-wave 506 that dP/dt 502 goes negative (passes through zero). It follows (from the discussion above) that the maximum dP/dt (PA diastolic pressure) occurs the first time after the R-wave 506 that $d^2P_{RV}/dt^2$ 504 goes negative.

FIG. 6A illustrates an actual human cardiac ECG waveform. The ECG P-wave 602 and R-wave 604 are obvious.

Looking now at FIG. 6B, actual cardiac waveforms of a patient's pulmonary artery (PA) pressure and right ventricular (RV) pressure are illustrated. From FIG. 6B it can be seen that the PA diastolic pressure (minimum PA) occurs at nearly the same pressure where the PA pressure and RV pressure signals cross each other.

FIG. 6C is the dP/dt waveform 606 resulting from a first derivative of the patient's RV pressure signal 12. It is important here to note that the peak of dP/dt waveform 606 occurs at the same time that the PA pressure 18 equals the RV pressure 12.

Referring again to FIG. 1, the PA systolic pressure 22 is determined by feeding the RV pressure sensor output 12 into a sample and hold circuit 34. The sample and hold circuit 34 is enabled by the sensing of the R-wave 506 shown in FIG. 5A. The systolic pressure 22 is then latched when dP/dt 502 illustrated in FIG. 5C goes negative as determined by comparator 36 output signal 28. This value of systolic pressure will be held until the next R-wave 506 is sensed, enabling the sample and hold circuit 34 to change values.

Figure 5D:
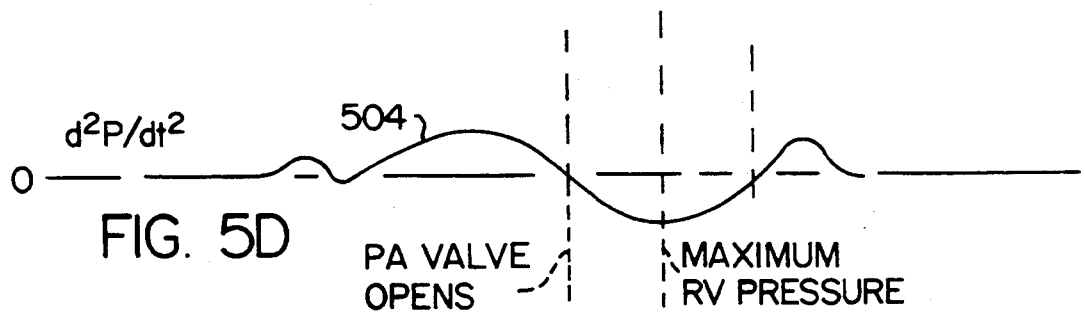
FIG. 5D illustrates a signal derived from the derivative of the signal depicted in FIG. 5C, and which can be used to determine pulmonary artery diastolic pressure.

Similarly, the PA diastolic pressure is determined by feeding the RV pressure 12 into a sample and hold circuit 32 which is latched by comparator 38 the first time that $d^2P_{RV}/dt^2$ 504 illustrated in FIG. 5D goes negative after a sensed R-wave 506. In this case, a short delay 30 in the pressure signal path balances the electronic delays in the two signal paths, keeping the timing synchronized.

From the above description of the present invention, it is apparent that numerous pressure readings other than those described hereinbefore, can be obtained with the present invention. For example, the present invention can be used to obtain right ventricular systolic and diastolic maximum dP/dt, etc.

Measurement of atrial pressures can also be accomplished similarly as follows. The right atrial (RA) systolic pressure 24, like PA systolic pressure 22, is latched by a sample and hold circuit 46. Unlike PA pressure measurements however, latching occurs the first time that dP/dt 502 passes through zero subsequent to detection of a P-wave 508 as depicted in FIG. 5A. RA diastolic pressure 20 is determined in the preferred embodiment shown in FIG. 1 by latching the RV pressure 12 at a time (eg. 100 msec) before the RA systolic pressure 24 measurement of interest. This is accomplished by delaying the RV pressure signal 12 with a delay circuit 48, and then latching the delayed signal with a sample and hold circuit 50 upon detection of a p-wave 508.

The preferred embodiment 10 described hereinbefore and illustrated in FIG. 1 is shown as pressure sensing circuit 10 in FIG. 2. Turning now to FIG. 2, there is illustrated in block diagram form, a complete implantable pressure telemetry system 200 for measurement and transmission of patient pulmonary and venous pressure values to an external communication device.

Although a particular implementation of a pulmonary and venous pressure measurement and telemetry system 200 is disclosed herein, it is to be understood that the present invention may be advantageously practiced in conjunction with many different types of telemetry systems.

Telemetry circuit 202 is schematically shown in FIG. 2 to be electrically coupled via P-wave/R-wave sensor leads 240, 246 and RV pressure sensor leads 404, 406 to a patient's heart 400. Leads 240, 246, 404, 406 can be of either the unipolar or bipolar type as is well known in the art; alternatively, a single, multiple-electrode lead may be used.

Telemetry system 200 contains the analog circuits 202 for interface to the heart 400, an antenna 230, and circuits (not shown, but conventional to those skilled in the art) for the detection of pressure signals from the heart It will be understood that each of the electrical components represented in FIG. 2 is powered by an appropriate implantable battery power source 206, in accordance with common practice in the art. For the sake of clarity, the coupling of battery power to the various components of telemetry circuit 202 has not been shown in the Figures.

An antenna 230 is connected to telemetry circuit 202 for purposes of uplink/downlink telemetry through an RF transmitter and receiver unit 224. Unit 224 may correspond to the telemetry and program logic employed in U.S. Pat. No. 4,556,063 issued to Thompson et al. on Dec. 3, 1985 and U.S. Pat. No. 4,257,423 issued to McDonald et al. on Mar. 24, 1981, both of which are incorporated herein by reference in their entirety. Telemetering analog and/or digital data between antenna 230 and an external device, such as the aforementioned external communication device (not shown in FIG. 2), may be accomplished in the presently disclosed embodiment by means of all data first being digitally encoded and then pulse-position modulated on a damped RF carrier, as substantially described in U.S. Pat. No. 5,127,404 issued to Wyborny et al entitled "Improved Telemetry Format", which is assigned to the assignee of the present invention and which is incorporated herein by reference in its entirety.

A crystal oscillator circuit 228, typically a 32,768 Hz crystal-controlled oscillator, provides main timing clock signals to digital controller/timer circuit 216. A $V_{REF}$ and Bias circuit 220 generates stable voltage reference and bias currents for the telemetry system 200 analog circuits. An analog-to-digital converter (ADC) and multiplexer unit 222 digitizes analog signals and voltages to provide "real-time" telemetry communication signals and battery end-of-life (EOL) replacement functions. A power-on-reset (POR) circuit 226 functions as a means to reset circuitry and related functions to a default condition upon detection of a low battery condition, which will occur upon initial device power-up or will transiently occur in the presence of electromagnetic interference, for example.

The timing functions of telemetry system 200 are controlled by event timer 204 in conjunction with digital controller/timer circuit 216 wherein digital timers and counters are employed to establish the overall event timing of the telemetry system 200, including timing windows for controlling the operation of the peripheral components within telemetry circuit 202.

Event timer 204 monitors the pressure event signals received from heart 400 by pressure sensing circuit 10, and handshakes with digital controller/timer circuit 216 on a bidirectional bus 208 to synchronize measurement of and rf transmission of the desired pressure signal values to an external communication device.

Digital controller/timer circuit 216 is coupled to pressure sensing circuit 10. In particular, digital controller/timer circuit 216 receives PA diastolic signal 18 on line 232, PA systolic signal 22 on line 234, RA diastolic signal 20 on line 238 and RA systolic signal 24 on line 226. P-wave and R-wave sense amplifiers (not shown) are coupled to leads 240 and 246, in order to receive ECG signals from heart 400. The sense amplifiers correspond, for example, to that disclosed in U.S. Pat. No. 4,379,459 issued to Stein on Apr. 12, 1983, incorporated by reference herein in its entirety.

Sense amplifier sensitivity control (also not shown) is provided to adjust the gain of sense amplifier circuitry in accordance with programmed sensitivity settings, as would be appreciated by those of ordinary skill in the pacing art.

While a specific embodiment of pressure sensing circuit 10 has been identified herein, this is done for the purposes of illustration only. It is believed by the inventor that the specific embodiment of such a circuit is not critical to the present invention so long as it provides means for temporarily storing PA and RA systolic and diastolic pressures and providing digital controller/timer circuit 216 with signals indicative of PA and RA systolic and diastolic pressures accordingly. It is also believed that those of ordinary skill in the art could choose from among the various well-known implementations of such circuits in practicing the present invention.

While the invention has been described above in connection with the particular embodiments and examples, one skilled in the art will appreciate that the invention is not necessarily so limited. It will thus be understood that numerous other embodiments, examples, uses, modifications of, and departures from the teachings disclosed may be made, without departing from the scope of the present invention as claimed herein.

What is claimed is:

1. A method of pressure monitoring employing an absolute pressure sensor, which provides an output signal having an amplitude which varies according to pressure, comprising:

implanting said absolute pressure sensor in said right ventricle of said patient;
deriving a first derivative of said output signal;
deriving a second derivative of said output signal;
providing said output signal to first, second and third holding means for storing signal amplitudes;
enabling said first holding means and said second holding means in response to occurrence of an R-wave;
thereafter storing a first output signal amplitude in said first holding means in response to said first derivative being less than zero, wherein said first stored output signal amplitude is equal to said patient's pulmonary artery systolic pressure and, storing a second output signal amplitude in said second holding means in response to said second derivative being less than zero, wherein said second stored output value is equal to said patient's pulmonary artery diastolic pressure;
enabling said third holding means in response to occurrence of a P-wave:
thereafter storing a third output signal amplitude in said third holding means in response to said first derivative being less than zero, wherein said third stored output signal amplitude is equal to said patient's right atrial systolic pressure;
delaying said output signal; and
storing an amplitude of said delayed output signal in a fourth holding means for storing signal amplitudes in response to occurrence of said P-wave, wherein said stored amplitude of said delayed output signal is equal to said patient's right atrial diastolic pressure.

2. A method of pressure monitoring employing an absolute pressure sensor, which provides an output signal having an amplitude which varies according to pressure, comprising:

implanting said absolute pressure sensor in said right ventricle of said patient;
deriving a first derivative of said output signal;
deriving a second derivative of said output signal;
providing said output signal to first and second holding means for storing signal amplitudes;
enabling said first and second holding means in response to occurrence of an R-wave; and
thereafter storing a first output signal amplitude in said first holding means in response to said first derivative being less than zero, wherein said first stored output signal amplitude is equal to said patient's pulmonary artery systolic pressure and storing a second output signal amplitude in said second holding means in response to said second derivative being less than zero, wherein said second stored output value is equal to said patient's pulmonary artery diastolic pressure.

3. A method of pressure monitoring employing an absolute pressure sensor, which provides an output signal having an amplitude which varies according to pressure, comprising:

implanting said absolute pressure sensor in said right ventricle of said patient;
deriving a first derivative of said output signal;
providing said output signal to a first holding means for storing signal amplitudes;
enabling said first holding means in response to occurrence of a P-wave:
thereafter storing a first output signal amplitude value in said first holding means in response to said first derivative value being less than zero, wherein said first stored output signal amplitude is equal to said patient's right atrial systolic pressure;
delaying said output signal; and
storing an amplitude of said delayed output signal in a second holding means for storing signal amplitudes in response to said P-wave, wherein said second stored output signal amplitude is equal to said patient's right atrial diastolic pressure.

4. A pressure monitoring system, comprising: an absolute pressure sensor means for providing an output signal having an amplitude which varies according to pressure, adapted to be implanted in a patient's right ventricle;

means for detecting R-waves;
means for detecting P-waves;
means for deriving a first derivative of said output signal;
means for deriving a second derivative of said output signal;
first holding means coupled to said pressure sensor, enabled in response to detection of an R-wave, for thereafter storing a first output signal amplitude in response to said first derivative being less than zero;
second holding means coupled to said pressure sensor, enabled in response to detection of an R-wave, for thereafter storing a second output signal amplitude in response to said second derivative being less than zero;
third holding means coupled to said pressure sensor, enabled in response to detection of an P-wave, for thereafter storing a third output signal amplitude in response to said first derivative being less than zero;
delay means coupled to said pressure sensor for providing a delayed output signal; and
fourth holding means coupled to delay means, for storing an amplitude of said delayed output signal in response to detection of a P-wave.

5. A pressure monitoring system, comprising:

an absolute pressure sensor means for providing an output signal having an amplitude which varies according to pressure, adapted to be implanted in a patient's right ventricle;
means for detecting R-waves;
means for deriving a first derivative of said output signal;
means for deriving a second derivative of said output signal;
first holding means coupled to said pressure sensor, enabled, in response to detection of an R-wave, for thereafter storing a first output signal amplitude in response to said first derivative being less than zero; and
second holding means coupled to said pressure sensor, enabled in response to detection of an R-wave, for thereafter storing a second output signal amplitude in response to said second derivative being less than zero.

6. A pressure monitoring system, comprising:

an absolute pressure sensor means for providing an output signal having an amplitude which varies according to pressure, adapted to be implanted in a patient's right ventricle;
means for detecting P-waves;
means for deriving a first derivative of said output signal;
first holding means coupled to said pressure sensor, enabled in response to detection of an P-wave, for thereafter storing a first output signal amplitude in response to said first derivative being less than zero;
delay means coupled to said pressure sensor for providing a delayed output signal; and
second holding means coupled to delay means, for storing an amplitude of said delayed output signal in response to detection of a P-wave.

* * * * *